United States Patent
Jeong et al.

(10) Patent No.: US 9,889,139 B2
(45) Date of Patent: Feb. 13, 2018

(54) METHOD OF TREATING INFLAMMATORY BOWEL DISEASE COMPRISING ADMINISTERING A PHARMACEUTICAL COMPOSITION COMPRISING A 6-AMINOPYRIDIN-3-OL COMPOUND OR A PHARMACEUTICALLY ACCEPTABLE SALT THEREOF AS AN ACTIVE INGREDIENT TO A SUBJECT

(71) Applicant: Research Cooperation Foundation of Yeungnam University, Gyeongsan-si, Gyeongsangbuk-do (KR)

(72) Inventors: Byeong Seon Jeong, Daegu (KR); Jung Ae Kim, Daegu (KR); Dong Guk Kim, Daegu (KR); You Ra Kang, Gyeongsan-si (KR); Tae Gyu Nam, Suwon-si (KR)

(73) Assignee: Research Cooperation Foundation of Yeungnam University, Gyeongsan-si, Gyeongsangbuk-do (KR)

( * ) Notice: Subject to any disclaimer, the term of this patent is extended or adjusted under 35 U.S.C. 154(b) by 0 days.

(21) Appl. No.: 15/237,642

(22) Filed: Aug. 16, 2016

(65) Prior Publication Data

US 2016/0354352 A1 Dec. 8, 2016

Related U.S. Application Data

(63) Continuation-in-part of application No. 14/367,237, filed as application No. PCT/KR2012/011302 on Dec. 21, 2012, now Pat. No. 9,452,159.

(30) Foreign Application Priority Data

Dec. 21, 2011 (KR) .......................... 10-2011-0139306
Dec. 20, 2012 (KR) .......................... 10-2012-0149669

(51) Int. Cl.
| | |
|---|---|
| A61K 31/5377 | (2006.01) |
| A61K 31/44 | (2006.01) |
| A61K 31/4439 | (2006.01) |
| A61K 31/496 | (2006.01) |
| A61K 31/4545 | (2006.01) |
| A61K 31/443 | (2006.01) |
| A61K 31/444 | (2006.01) |
| A61K 31/4412 | (2006.01) |

(52) U.S. Cl.
CPC ...... *A61K 31/5377* (2013.01); *A61K 31/4412* (2013.01); *A61K 31/496* (2013.01)

(58) Field of Classification Search
CPC ...... A61P 25/00; A61P 29/00; A61K 31/4402; C07D 213/74

USPC ........................................................ 514/235.5
See application file for complete search history.

(56) References Cited

U.S. PATENT DOCUMENTS

| | | | | |
|---|---|---|---|---|
| 5,001,136 A | * | 3/1991 | Walker ................. | C07D 213/74 514/336 |
| 9,452,159 B2 | * | 9/2016 | Jeong ................... | C07D 213/74 |
| 9,505,757 B2 | * | 11/2016 | Jeong ................... | A61K 9/2018 |
| 2008/0227776 A1 | | 9/2008 | Oates et al. | |
| 2015/0031890 A1 | | 1/2015 | Jeong et al. | |
| 2015/0320729 A1 | | 11/2015 | Jeong et al. | |
| 2016/0068489 A1 | | 3/2016 | Jeong et al. | |

FOREIGN PATENT DOCUMENTS

| | | |
|---|---|---|
| JP | 2011032210 A | 2/2011 |
| WO | 2004-004720 A1 | 1/2004 |
| WO | 2010-086646 A1 | 8/2010 |
| WO | WO2013085340 * | 6/2013 |

OTHER PUBLICATIONS

Banskota; Bioorganic & Medicinal Chemistry Letters 2016, 26, 4587-4591.*
Morampudi; Journal of Visualized Experiments 2014, 84, e51297, 1-8.*
Williams; Ther Adv Gastroenterol 2011, 4, 237-248.*
PubChemCompound, datasheet [online compound summary] Retrieved from the Internet: <URL: http://pubchem.ncbi.nlm.nih.gov/search/search.cgi> CID 23292067, CID 17819954, CID 23145495, CID 23145410, CID 23145727 etc., Dated Dec. 2007.
A.A.Sologub et al., "Emoxypine as an inhibitor of angiogenesis", Bulletin of Experimental Biology and Medicine, 1992, vol. 114, No. 6, pp. 1827-1830.
De Angelis; Bioorganic & Medicinal Chemistry Letters 14 (2004) 5835-5839.
Nam; Org. Biomol. Chem., 2009, 7, 5103-5112.
Serwa; Chem. Eur. J. 2010, 16, 14106-14114.
Simone, Oncology: Introduction, Cecil Textbook of Medicine, 20th Edition, 1996 vol. 1, pp, 1004-1010.
Johnson; British Journal of Cancer 2001, 84, 1424-1431.
Ribatti; Pharmaceuticals 2010, 3, 482-513.
Omata; Free Radical Biology & Medicine 2010, 48, 1358-1365.
Arce; Bioorganic & Medicinal Chemistry 2012, 20, 5188-5201.
Kim; European Journal of Medicinal Chemistry 2014, 78, 126-139.

* cited by examiner

*Primary Examiner* — Daniel Carcanague
(74) *Attorney, Agent, or Firm* — Revolution IP, PLLC

(57) ABSTRACT

Provided is a method of treating inflammatory bowel disease comprising administering a pharmaceutical composition comprising a 6-aminopyridin-3-ol compound or a pharmaceutically acceptable salt thereof as an active ingredient to a subject, which inhibits colitis in a model of inflammatory bowel disease, and accordingly, they may be suitable for use as a drug for the prevention or treatment of inflammatory bowel disease.

6 Claims, No Drawings

METHOD OF TREATING INFLAMMATORY BOWEL DISEASE COMPRISING ADMINISTERING A PHARMACEUTICAL COMPOSITION COMPRISING A 6-AMINOPYRIDIN-3-OL COMPOUND OR A PHARMACEUTICALLY ACCEPTABLE SALT THEREOF AS AN ACTIVE INGREDIENT TO A SUBJECT

CROSS REFERENCE TO PRIOR APPLICATION

This application is a Continuation-In-Part Application of U.S. patent application Ser. No. 14/367,237 filed on Jun. 20, 2014 under 35 U.S.C. §120, which is the 35 U.S.C. §371 national stage of International application PCT/KR2012/011302 filed on Dec. 21, 2012, which claims priority to Korean applications 10-2011-0139306 and 10-2012-0149669 filed on Dec. 21, 2011 and Dec. 20, 2012, respectively.

BACKGROUND

The present invention relates to a method of treating inflammatory bowel disease comprising administering a pharmaceutical composition comprising a 6-aminopyridin-3-ol compound or a pharmaceutically acceptable salt thereof as an active ingredient to a subject.

Angiogenesis is the process through which new capillary vessels form from existing micro vessels. Angiogenesis normally occurs during embryonic development, tissue regeneration, wound healing, and corpus luteum development that is a cyclic change of female reproductive system, and even in these cases, angiogenesis occurs under stringent control.

For adults, endothelial cells very slowly grow, and compared to other kinds of cells, they do not divide well. Angiogenesis occurs such that in general, due to the stimulus of a promotion factor for angiogenesis, vascular basal membrane decomposes by protease, and endothelial cells move, proliferate, and differentiate, leading to formation of lumen and reconstruction of vessels, forming new capillary vessels.

However, in some cases, angiogenesis may not be autonomously controlled but pathologically grows to cause disease. Examples of angiogenesis-associated disease that occurs in a pathologic state are hemangioma, angiofibroma, vascular malformation, and cardiovascular disease, such as arteriosclerosis, vascular adhesion, or scleroedema, and examples of angiogenesis-associated ophthalmic disease are keratoplasty angiogenesis, angiogenic glaucoma, diabetic retinopathy, neovascular corneal disease, macular degeneration, pterygium, retinal degeneration, retrolental fibroplasia, and trachoma. Chronic inflammatory disease, such as arthritis, dermatology disease, such as acne, psoriasis, capillarectasia, granuloma pyogenicum, or dermatitis seborrheica, Alzheimer's disease, and obesity are also associated with angiogenesis, and the growth and metastasis of cancer are necessarily dependent on angiogenesis.

In particular, in the case of cancer, angiogenesis plays a critical role in the growth and metastasis of cancer cells. Tumors are fed with nutrition and oxygen required for the growth and proliferation through new blood vessels, and new blood vessels permeated into tumor allow metastasizing cancer cells to enter a blood circulation system, causing metastasis of cancer cells. The major death cause of cancer patients is metastasis, which often leads to the failure of clinical chemotherapy or immuno-therapy performed to increase survival rate of cancer patients.

Arthritis, which is a representative inflammatory disease, is caused by abnormal autoimmune system. However, when the disease progresses, chronic inflammation developed in synovial cavity between joints induces angiogenesis and destroys cartilage. That is, cytokines inducing inflammation help proliferation of synovial cells and vascular endothelial cells in synovial cavity, and while angiogenesis progresses, joint pannus, which is a connective tissue occurring in a cartilage site, is formed to destroy cartilage acting as a cushion.

Each year, many ophthalmic diseases cause blindness in hundreds of people worldwide, and induce angiogenesis. Representative examples of such diseases are macular degeneration, which occurs in old people, diabetic retinopathy, premature infant retinopathy, neovascular glaucoma, and corneal disease caused by neovascularization cause angiogenesis. From among these disease, diabetic retinopathy is a complication of diabetes that causes blindness by invasiveness of retinal capillary vessels into hyaloid.

Psoriasis characterized with red spots and scaly skin is also a chronic proliferative disease that develops in the skin. Psoriasis is not treatable and accompanies pains and malformation. In a normal case, horny cells proliferate once a month. However, in the case of psoriasis patients, horny cells proliferate at least once a week. This rapid proliferation needs much blood, which is why angiogenesis actively occurs.

Angiogenesis inhibitors can be used as a therapeutic agent for these angiogenesis-associated diseases. Accordingly, research into how to treat these diseases by inhibiting angiogenesis is actively being performed. In general, angiogenesis inhibitors are administered to patients for a long period of time, so that they desirably need to be non-toxic and orally administrable. Accordingly, there is a need to develop as an angiogenesis inhibitor a drug whose toxicity is negligible.

SUMMARY

In response, the inventors of the present application confirmed that 6-aminopyridin-3-ol derivatives each having a particular structure or pharmaceutically acceptable salts thereof has excellent inflammatory bowel disease treating effects, thereby completing the present invention.

Accordingly, the purpose of the present invention is to provide a method of treating inflammatory bowel disease comprising administering a pharmaceutical composition comprising a 6-aminopyridin-3-ol compound or a pharmaceutically acceptable salt thereof as an active ingredient to a subject.

The present invention provides a method of treating inflammatory bowel disease, comprising:

administering a pharmaceutical composition comprising a 6-aminopyridin-3-ol compound of Formula 1 below or a pharmaceutically acceptable salt thereof as an active ingredient to a subject:

[Formula 1]

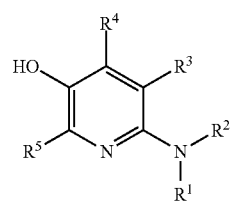

wherein
R¹ is a hydrogen, a C1 to C4 alkyl, or a phenyl, R² is a hydrogen, a C1 to C16 alkyl, a C1 to C16 hydroxyalkyl, a C2 to C4 (5-hydroxy-trimethylpyridin-2-yloxy)alkyl, a C3 to C7 cycloalkyl, a benzyl, a phenyl, a C1 to C4 alkylphenyl, a nitrophenyl, a halophenyl, a benzo[d][1,3]-dioxol-5-yl, or a pyridine-2-yl; or R¹ and R² are linked to each other to form a 5-membered ring or a 6-membered ring, thereby forming a heterocyclic compound, and are any one selected from pyrrolidine-1-yl, 4-methylpiperazine-1-yl, 6-morpholino, and 1H-pyrrol-1-yl, and each of R³ to R⁵ is a methyl.

6-aminopyridin-3-ol derivatives or pharmaceutically acceptable salts thereof according to the present invention inhibit colitis in a model of inflammatory bowel disease, and accordingly, they may be suitable for use as a drug for the prevention or treatment of inflammatory bowel disease.

The present invention provides a method of treating inflammatory bowel disease, comprising:
administering a pharmaceutical composition comprising a 6-aminopyridin-3-ol compound of Formula 1 below or a pharmaceutically acceptable salt thereof as an active ingredient to a subject:

[Formula 1]

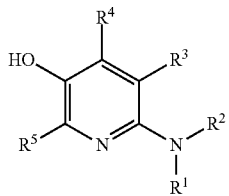

wherein
R¹ is a hydrogen, a C1 to C4 alkyl, or a phenyl, R² is a hydrogen, a C1 to C16 alkyl, a C1 to C16 hydroxyalkyl, a C2 to C4 (5-hydroxy-trimethylpyridin-2-yloxy)alkyl, a C3 to C7 cycloalkyl, a benzyl, a phenyl, a C1 to C4 alkylphenyl, a nitrophenyl, a halophenyl, a benzo[d][1,3]-dioxol-5-yl, or a pyridine-2-yl; or R¹ and R² are linked to each other to form a 5-membered ring or a 6-membered ring, thereby forming a heterocyclic compound, and are any one selected from pyrrolidine-1-yl, 4-methylpiperazine-1-yl, 6-morpholino, and 1H-pyrrol-1-yl, and each of R³ to R⁵ is a methyl.

In some embodiments, in the formula representing the compound, R¹ may be a hydrogen, a C1 to C4 alkyl, or a phenyl, R² may be a hydrogen, a C6 to C16 alkyl, a C1 to C6 hydroxyalkyl, (5-hydroxy-3,4,6-trimethylpyridin-2-yloxy)propyl, a C5 to C6 cycloalkyl, a benzyl, a phenyl, a C1 to C4 alkylphenyl, a nitrophenyl, a halophenyl, or a benzo[d][1,3]-dioxol-5-yl or pyridine-2-yl; or R¹ and R² are linked to each other to form a 5-membered ring to a 6-membered ring, thereby forming a heterocyclic compound, and are each pyrrolidine-1-yl, 4-methylpiperazine-1-yl, 6-morpholino, or 1H-pyrrol-1-yl, and each of R³ to R⁵ may be a methyl.

In some embodiments, the compound or pharmaceutically acceptable salt thereof may be selected from 6-amino-2,4,5-trimethylpyridin-3-ol; 6-(hexylamino)-2,4,5-trimethylpyridin-3-ol; 6-(hexadecylamino)-2,4,5-trimethylpyridin-3-ol; 6-(benzylamino)-2,4,5-trimethylpyridin-3-ol; 6-((3-hydroxypropyl)amino)-2,4,5-trimethylpyridin-3-ol; 6-(3-((5-hydroxy-3,4,6-trimethylpyridin-2-yl)amino)propoxy)-2,4,5-trimethylpyridin-3-ol; 6-(cyclopentylamino)-2,4,5-trimethylpyridin-3-ol; 6-(cyclohexylamino)-2,4,5-trimethylpyridin-3-ol; 2,4,5-trimethyl-6-(phenylamino) pyridin-3-ol; 2,4,5-trimethyl-6-(m-tolylamino)pyridin-3-ol; 2,4,5-trimethyl-6-(p-tolylamino)pyridin-3-ol; 2,4,5-trimethyl-6-((4-propylphenyl)amino)pyridin-3-ol; 6-((2-isopropylphenyl)amino)-2,4,5-trimethylpyridin-3-ol; 6-((4-(tert-butyl)phenyl)amino)-2,4,5-trimethylpyridin-3-ol; 6-((4-methoxyphenyl)amino)-2,4,5-trimethylpyridin-3-ol; 6-((3-isopropoxyphenyl)amino)-2,4,5-trimethylpyridin-3-ol; 6-(benzo[d][1,3]dioxol-5-ylamino)-2,4,5-trimethylpyridin-3-ol; 6-((3-fluorophenyl)amino)-2,4,5-trimethylpyridin-3-ol; 6-((4-fluorophenyl)amino)-2,4,5-trimethylpyridin-3-ol; 6-((3-chlorophenyl)amino)-2,4,5-trimethylpyridin-3-ol; 6-((4-chlorophenyl)amino)-2,4,5-trimethylpyridin-3-ol; 6-((3-bromophenyl)amino)-2,4,5-trimethylpyridin-3-ol; 6-((4-bromophenyl)amino)-2,4,5-trimethylpyridin-3-ol; 2,4,5-trimethyl-6-((3-nitrophenyl)amino)pyridin-3-ol; 2,4,5-trimethyl-6-((4-nitrophenyl)amino)pyridin-3-ol; 2,4,5-trimethyl-6-(pyridin-2-ylamino)pyridin-3-ol; 2,4,5-trimethyl-6-(pyrrolidin-1-yl)pyridin-3-ol; 2,4,5-trimethyl-6-(piperidin-1-yl)pyridin-3-ol; 2,4,5-trimethyl-6-(4-methylpiperazin-1-yl)pyridin-3-ol; 2,4,5-trimethyl-6-morpholinopyridin-3-ol; 2,4,5-trimethyl-6-(methyl(phenyl)amino)pyridin-3-ol; 2,4,5-trimethyl-6-(methyl(m-tolyl)amino)pyridin-3-ol; 2,4,5-trimethyl-6-(methyl(p-tolyl)amino)pyridin-3-ol; 6-((4-fluorophenyl)(methyl)amino)-2,4,5-trimethylpyridin-3-ol; 6-((4-chlorophenyl)(methyl)amino)-2,4,5-trimethylpyridin-3-ol; 6-(diphenylamino)-2,4,5-trimethylpyridin-3-ol; 2,4,5-trimethyl-6-(methyl(pyridin-2-yl)amino)pyridin-3-ol and 2,4,5-trimethyl-6-(1H-pyrrol-1-yl)pyridin-3-ol.

The pharmaceutically acceptable salt may be an acid-added salt formed from either an organic acid selected from the group consisting of an oxalic acid, a maleic acid, a fumaric acid, a malic acid, a tartaric acid, a citric acid, a benzoic acid, methanesulfonic acid and camphorsulfonic acid, or an inorganic acid selected from the group consisting of a hydrochloric acid, a sulfuric acid, a phosphoric acid, and a hydrobromic acid.

The amount and use method of the pharmaceutical composition may vary according to formulation and purpose.

The pharmaceutical composition according to the present invention may include the 6-aminopyridin-3-ol compound or pharmaceutically acceptable salt thereof in an amount of 0.1 to 50 wt % based on the total weight of the composition.

In some embodiments, the pharmaceutical composition according to the present invention may further include a carrier, an excipient, and a diluent which are conventionally used in preparing a pharmaceutical composition.

Examples of the carrier, the excipient, and the diluent are lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, and mineral oil.

The pharmaceutical composition according to the present invention may be prepared in various formulations according to various conventional methods. For example, the pharmaceutical composition may be prepared in an oral formulation, an external-use formulation, a suppository formulation, or a sterile injection formulation. The oral formulation may be powder, granule, tablet, capsule, suspension, emulsion, syrup, or aerosols.

During preparation, a diluent or an excipient, such as fillers, thickeners, binders, wetting agents, disintegrants, or surfactants, may be used. For use as a solid preparation for oral administration, tablets, pills, powders, granules, capsules and so on are included, and these solid preparations may be prepared by mixing with at least one of the abovementioned compounds, for example, starch, calcium carbonate, sucrose, or lactose, or gelatin.

In addition to the simple excipient, lubricants, such as magnesium stearate and talc, may also be used herein. A liquid preparation for oral administration may be a suspension, a liquid for internal use, an emulsion, or a syrup, and includes various excipients, such as, for example, a wetting agent, a sweetening agent, an aromatic and a preservative, in addition to simple diluents such as water and liquid paraffin widely used in the art. A preparation for non-oral administration includes a sterile aqueous solution, a non-aqueous solvent, a suspension, an emulsion, a lyophilized preparation, or a suppository. A vegetable oil such as propylene glycol, polyethylene glycol, or olive oil, or an injectable ester such as ethyl oleate may be used as the non-aqueous solvent or suspension. A base of the suppository that may be used herein may include witepsol, macrogol, Tween 61, cacao butter, laurin butter or glycerogelatin.

The dosage of 6-aminopyridin-3-ol compound or pharmaceutically acceptable salt thereof according to the present invention may vary according to the age, gender, or body weight of a patient, and may be in a range of 0.001 to 100 mg/kg, for example, 0.01 to 10 mg/kg, and these ranges of amount may be administered once a day or may be divided into several portions which are then separately administered within a day. The dosage of 6-aminopyridine-3-ol compound or pharmaceutically acceptable salt thereof may vary according to administration passage, severity of disease, gender, body weight, age, or the like. Accordingly, the dosage, in any aspects, does not limit the scope of the present invention.

The pharmaceutical composition may be administered to rats, mice, livestock, humans, or the like thorough various administration routes. All of these administration routes are expectable, and for example, the composition may be administered orally, rectally, intravenously, muscularly, subcutaneously, intrauterine-subdurally or intracerebroventricularly.

The 6-aminopyridin-3-ol compound or pharmaceutically acceptable salt thereof according to the present invention has a 50% lethal amount ($LC_{50}$) of 2 g/kg or more, thereby having safety. Accordingly, the 6-aminopyridine-3-ol compound or pharmaceutically acceptable salt thereof according to the present invention can be used in a pharmaceutical composition according to the present invention.

DETAILED DESCRIPTION

Hereinafter, embodiments of the present invention will be described herein. However, the embodiments do not limit the present invention.

<Example 1> Preparation of Aminopyridinols

[Synthetic Method A]

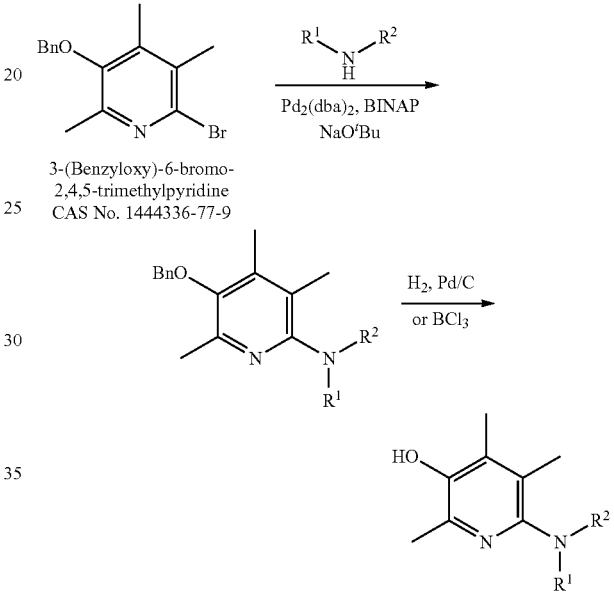

3-(Benzyloxy)-6-bromo-
2,4,5-trimethylpyridine
CAS No. 1444336-77-9

TABLE 1

| Compound No. | CAS No. | Reference or Synthetic method |
|---|---|---|
| 01 | 1245315-08-5 | European Journal of Medicinal Chemistry (2014), 78, 126-139. PCT Int. Appl. (2013), WO 2013095060 A1 20130627. |
| 02 | 1245315-10-9 | European Journal of Medicinal Chemistry (2014), 78, 126-139. PCT Int. Appl. (2013), WO 2013095060 A1 20130627. |
| 03 | 1245315-11-0 | European Journal of Medicinal Chemistry (2014), 78, 126-139. PCT Int. Appl. (2013), WO 2013095060 A1 20130627. |
| 04 | 1444333-80-5 | European Journal of Medicinal Chemistry (2014), 78, 126-139. PCT Int. Appl. (2013), WO 2013095060 A1 20130627. |
| 05 | 1444333-54-3 | European Journal of Medicinal Chemistry (2014), 78, 126-139. PCT Int. Appl. (2013), WO 2013095060 A1 20130627. |
| 06 | 1444333-62-3 | European Journal of Medicinal Chemistry (2014), 78, 126-139. PCT Int. Appl. (2013), WO 2013095060 A1 20130627. |
| 07 | Unknown | Synthetic method A $^1$H NMR (400 MHz, CDCl$_3$) δ 5.20-4.44 (m, 1H), 4.35-4.21 (m, 1H), 2.31 (s, 3H), 2.11 (s, 3H), 2.17-1.87 (m, 2H), 1.93 (s, 3H), 1.72-1.61 (m, 2H), 1.61-1.50 (m, 2H), 1.37-1.26 (m, 2H). |
| 08 | 1444333-71-4 | European Journal of Medicinal Chemistry (2014), 78, 126-139. PCT Int. Appl. (2013), WO 2013095060 A1 20130627. |
| 09 | 1444333-89-4 | European Journal of Medicinal Chemistry (2014), 78, 126-139. PCT Int. Appl. (2013), WO 2013095060 A1 20130627. |
| 10 | Unknown | Synthetic method A $^1$H NMR (400 MHz, CD$_3$OD) δ 7.00 (t, J = 7.7 Hz, 1H), 6.73-6.63 (m, 2H), 6.56 (d, J= 7.4 Hz, 1H), 2.34 (s, 3H), 2.22 (s, 3H), 2.21 (s, 3H), 2.09 (s, 3H). |

TABLE 1-continued

| Compound No. | CAS No. | Reference or Synthetic method |
|---|---|---|
| 11 | Unknown | Synthetic method A<br>$^1$H NMR (400 MHz, CD$_3$OD) δ 6.96-6.91 (m, 2H), 6.85-6.80 (m, 2H), 2.33 (s, 3H), 2.20 (s, 3H), 2.19 (s, 3H), 2.07 (s, 3H). |
| 12 | Unknown | Synthetic method A<br>$^1$H NMR (250 MHz, (CD$_3$)$_2$SO) δ 8.56 (br s, 1H), 7.90 (br s, 1H), 7.13 (d, J = 8.3 Hz, 2H), 7.01 (d, J = 8.4 Hz, 2H), 2.44 (d, J = 7.5 Hz, 2H), 2.31 (s, 3H), 2.19 (s, 3H), 2.10 (s, 3H), 1.62-1.46 (m, 2H), 0.88 (t, J = 7.3 Hz, 3H). |
| 13 | 1444334-07-9 | European Journal of Medicinal Chemistry (2014), 78, 126-139.<br>PCT Int. Appl. (2013), WO 2013095060 A1 20130627. |
| 14 | Unknown | Synthetic method A<br>$^1$H NMR (250 MHz, (CD$_3$)$_2$SO) δ 7.91 (s, 1H), 7.37 (s, 1H), 7.27-7.12 (m, 4H), 2.26 (s, 3H), 2.13 (s, 3H), 2.08 (s, 3H), 1.25 (s, 9H). |
| 15 | Unknown | Synthetic method A<br>$^1$H NMR (400 MHz, CD$_3$OD) δ 6.97-6.93 (m, 2H), 6.79-6.74 (m, 2H), 3.72 (s, 3H), 2.31 (s, 3H), 2.20 (s, 3H), 2.08 (s, 3H). |
| 16 | Unknown | Synthetic method A<br>$^1$H NMR (250 MHz, (CD$_3$)$_2$SO) δ 7.46 (s, 1H), 7.04-6.95 (m, 2H), 6.81-6.75 (m, 1H), 6.31-6.23 (m, 1H), 4.48 (dq, J = 12.1, 6.0 Hz, 1H), 2.28 (s, 3H), 2.13 (s, 3H), 2.08 (s, 3H), 1.25 (d, J = 6.0 Hz, 6H). |
| 17 | 1444334-34-2 | European Journal of Medicinal Chemistry (2014), 78, 126-139.<br>PCT Int. Appl. (2013), WO 2013095060 A1 20130627. |
| 18 | Unknown | Synthetic method A<br>$^1$H NMR (400 MHz, CD$_3$OD) δ 7.14-7.04 (m, 1H), 6.72-6.63 (m, 2H), 6.47-6.37 (m, 1H), 2.35 (s, 3H), 2.22 (s, 3H), 2.13 (s, 3H). |
| 19 | Unknown | Synthetic method A<br>$^1$H NMR (400 MHz, CD$_3$OD) δ 7.00-6.93 (m, 2H), 6.91-6.83 (m, 2H), 2.32 (s, 3H), 2.20 (s, 3H), 2.10 (s, 3H). |
| 20 | Unknown | Synthetic method A<br>$^1$H NMR (400 MHz, CD$_3$OD) δ 7.06 (t, J = 8.1 Hz, 1H), 6.95 (t, J = 2.1 Hz, 1H), 6.80 (ddd, J = 8.3, 2.2, 0.9 Hz, 1H), 6.68 (ddd, J = 7.9, 2.0, 0.9 Hz, 1H), 2.35 (s, 3H), 2.21 (s, 3H), 2.11 (s, 3H). |
| 21 | Unknown | Synthetic method A<br>$^1$H NMR (400 MHz, CD$_3$OD) δ 7.13-7.04 (m, 2H), 6.96-6.87 (m, 2H), 2.34 (s, 3H), 2.20 (s, 3H), 2.10 (s, 3H). |
| 22 | Unknown | Synthetic method A<br>$^1$H NMR (400 MHz, CD$_3$OD) δ 7.14 (t, J = 2.0 Hz, 1H), 7.04 (t, J = 8.0 Hz, 1H), 6.92-6.83 (m, 2H), 2.38 (d, J = 5.3 Hz, 3H), 2.25 (s, 3H), 2.15 (s, 3H). |
| 23 | 1444334-25-1 | European Journal of Medicinal Chemistry (2014), 78, 126-139.<br>PCT Int. Appl. (2013), WO 2013095060 A1 20130627. |
| 24 | Unknown | Synthetic method A<br>$^1$H NMR (400 MHz, CD$_3$OD) δ 7.93-7.90 (m, 1H), 7.59-7.54 (m, 1H), 7.35-7.32 (m, 2H), 2.37 (s, 3H), 2.24 (s, 3H), 2.16 (s, 3H). |
| 25 | 1444334-16-0 | European Journal of Medicinal Chemistry (2014), 78, 126-139.<br>PCT Int. Appl. (2013), WO 2013095060 A1 20130627. |
| 26 | Unknown | Synthetic method A<br>$^1$H NMR (400 MHz, (CD$_3$)$_2$SO) δ 8.33-8.20 (m, 2H), 8.08-8.01 (m, 1H), 7.55-7.46 (m, 1H), 7.23-7.13 (m, 1H), 6.73-6.64 (m, 1H), 2.30 (s, 3H), 2.14 (s, 3H), 2.07 (s, 3H) |
| 27 | 1444334-53-5 | European Journal of Medicinal Chemistry (2014), 78, 126-139.<br>PCT Int. Appl. (2013), WO 2013095060 A1 20130627. |
| 28 | Unknown | Synthetic method A<br>$^1$H NMR (400 MHz, CD$_3$OD) δ 2.92-2.84 (m, 4H), 2.32 (s, 3H), 2.15 (s, 3H), 2.14 (s, 3H), 1.72-1.61 (m, 4H), 1.61-1.49 (m, 2H). |
| 29 | 1444334-62-6 | European Journal of Medicinal Chemistry (2014), 78, 126-139.<br>PCT Int. Appl. (2013), WO 2013095060 A1 20130627. |
| 30 | 1444334-71-7 | European Journal of Medicinal Chemistry (2014), 78, 126-139.<br>PCT Int. Appl. (2013), WO 2013095060 A1 20130627. |
| 31 | Unknown | Synthetic method A<br>$^1$H NMR (400 MHz, CD$_3$OD) δ 7.15-7.05 (m, 2H), 6.69-6.60 (m, 1H), 6.46-6.38 (m, 2H), 3.19 (s, 3H), 2.38 (s, 3H), 2.22 (s, 3H), 1.98 (s, 3H). |
| 32 | Unknown | Synthetic method A<br>$^1$H NMR (400 MHz, CD$_3$OD) δ 6.98 (t, J = 7.8 Hz, 1H), 6.48 (d, J = 7.4 Hz, 1H), 6.26 (s, 1H), 6.21 (dd, J = 8.2, 2.3 Hz, 1H), 3.18 (s, 3H), 2.38 (s, 3H), 2.21 (d, J = 6.9 Hz, 6H), 1.96 (s, 3H). |
| 33 | Unknown | Synthetic method A<br>$^1$H NMR (400 MHz, CD$_3$OD) δ 6.95-6.90 (m, 2H), 6.37-6.32 (m, 2H), 3.18 (s, 3H), 2.38 (s, 3H), 2.20 (s, 3H), 2.18 (s, 3H), 1.95 (s, 3H). |
| 34 | Unknown | Synthetic method A<br>$^1$H NMR (400 MHz, CD$_3$OD) δ 6.91-6.78 (m, 2H), 6.45-6.35 (m, 2H), 3.18 (s, 3H), 2.37 (s, 3H), 2.22 (s, 3H), 1.99 (s, 3H). |
| 35 | Unknown | Synthetic method A<br>$^1$H NMR (400 MHz, CD$_3$OD) δ 7.11-7.02 (m, 2H), 6.43-6.34 (m, 2H), 3.19 (s, 3H), 2.38 (s, 3H), 2.23 (s, 3H), 1.99 (s, 3H). |

TABLE 1-continued

| Compound No. | CAS No. | Reference or Synthetic method |
|---|---|---|
| 36 | 1444334-44-4 | European Journal of Medicinal Chemistry (2014), 78, 126-139. PCT Int. Appl. (2013), WO 2013095060 A1 20130627. |
| 37 | 1444334-89-7 | European Journal of Medicinal Chemistry (2014), 78, 126-139. PCT Int. Appl. (2013), WO 2013095060 A1 20130627. |
| 38 | 1444334-80-8 | European Journal of Medicinal Chemistry (2014), 78, 126-139. PCT Int. Appl. (2013), WO 2013095060 A1 20130627. |

Compound 01

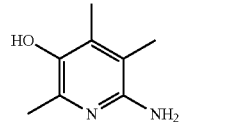

6-amino-2,4,5-trimethylpyridin-3-ol

Compound 02

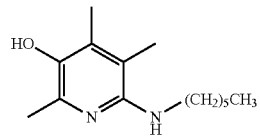

6-(hexylamino)-2,4,5-trimethylpyridin-3-ol

Compound 03

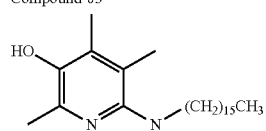

6-(hexadecylamino)-2,4,5-trimethylpyridin-3-ol

Compound 04

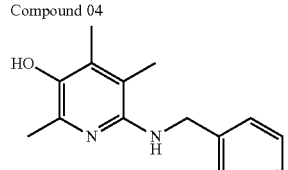

6-(benzylamino)-2,4,5-trimethylpyridin-3-ol

Compound 05

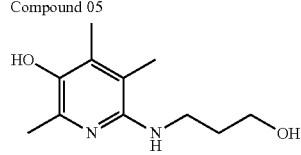

6-((3-hydroxypropyl)amino)-2,4,5-trimethylpyridin-3-ol

Compound 06

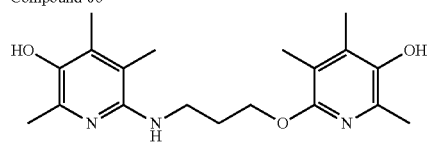

6-(3-((5-hydroxy-3,4,6-trimethylpyridin-2-yl)amino)propoxy)-2,4,5-trimethylpyridin-3-ol Compound 07

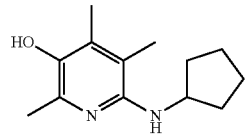 [SMILES: Cc1nc(NC2CCCC2)c(C)c(C)c1O]

6-(cyclopentylamino)-2,4,5-trimethylpyridin-3-ol

Compound 08

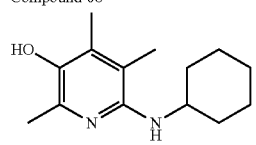

6-(cyclohexylamino)-2,4,5-trimethylpyridin-3-ol

TABLE 1-continued

| Compound No. | CAS No. | Reference or Synthetic method |
|---|---|---|

Compound 09

2,4,5-trimethyl-6-(phenylamino)pyridin-3-ol

Compound 10

2,4,5-trimethyl-6-(m-tolylamino)pyridin-3-ol

Compound 11

2,4,5-trimethyl-6-(p-tolylamino)pyridin-3-ol

Compound 12

2,4,5-trimethyl-6-((4-propylphenyl)amino)pyridin-3-ol

Compound 13

6-((2-isopropylphenyl)amino)-2,4,5-trimethylpyridin-3-ol

Compound 14

6-((4-(tert-butyl)phenyl)amino)-2,4,5-trimethylpyridin-3-ol

Compound 15

6-((4-methoxyphenyl)amino)-2,4,5-trimethylpyridin-3-ol

Compound 16

6-((3-isopropoxyphenyl)amino)-2,4,5-trimethylpyridin-3-ol

TABLE 1-continued

| Compound No. | CAS No. | Reference or Synthetic method |
|---|---|---|

Compound 17

6-(benzo[d][1,3]dioxol-5-ylamino)-2,4,5-trimethylpyridin-3-ol

Compound 18

6-((3-fluorophenyl)amino)-2,4,5-trimethylpyridin-3-ol

Compound 19

6-((4-fluorophenyl)amino)-2,4,5-trimethylpyridin-3-ol

Compound 20

6-((3-chlorophenyl)amino)-2,4,5-trimethylpyridin-3-ol

Compound 21

6-((4-chlorophenyl)amino)-2,4,5-trimethylpyridin-3-ol

Compound 22

6-((3-bromophenyl)amino)-2,4,5-trimethylpyridin-3-ol

Compound 23

6-((4-bromophenyl)amino)-2,4,5-trimethylpyridin-3-ol

Compound 24

2,4,5-trimethyl-6-((3-nitrophenyl)amino)pyridin-3-ol

Compound 25

2,4,5-trimethyl-6-((4-nitrophenyl)amino)pyridin-3-ol

TABLE 1-continued

| Compound No. | CAS No. | Reference or Synthetic method |
|---|---|---|

Compound 26

2,4,5-trimethyl-6-(pyridin-2-ylamino)pyridin-3-ol

Compound 27

2,4,5-trimethyl-6-(pyrrolidin-1-yl)pyridin-3-ol

Compound 28

2,4,5-trimethyl-6-(piperidin-1-yl)pyridin-3-ol

Compound 29

2,4,5-trimethyl-6-(4-methylpiperazin-1-yl)pyridin-3-ol

Compound 30

2,4,5-trimethyl-6-morpholinopyridin-3-ol

Compound 31

2,4,5-trimethyl-6-(methyl(phenyl)amino)pyridin-3-ol

Compound 32

2,4,5-trimethyl-6-(methyl(m-tolyl)amino)pyridin-3-ol

Compound 33

2,4,5-trimethyl-6-(methyl(p-tolyl)amino)pyridin-3-ol

TABLE 1-continued

| Compound No. | CAS No. | Reference or Synthetic method |
|---|---|---|

Compound 34

6-((4-fluorophenyl)(methyl)amino)-2,4,5-trimethylpyridin-3-ol

Compound 35

6-((4-chlorophenyl)(methyl)amino)-2,4,5-trimethylpyridin-3-ol

Compound 36

6-(diphenylamino)-2,4,5-trimethylpyridin-3-ol

Compound 37

2,4,5-trimethyl-6-(methyl(pyridin-2-yl)amino)pyridin-3-ol

Compound 38

2,4,5-trimethyl-6-(1H-pyrrol-1-yl)pyridin-3-ol

<Experimental Example 1> Test for Inhibitory Activity of Monocyte Against Adhesion to Intestinal Epithelial Cells 1. Test Method HT-29 human colon cancer cell-derived epithelial cells and U937 human-derived mononuclear cells were cultured at a temperature of 37° C. in the presence of 5% CO2 in an RPMI 1640 medium supplemented with 10% FBS and 1% penicillin/streptomycin (PS). When the cells were grown in the medium at a density of 80% or more, the cells were subjected to a subculture process with a ratio of 1:3 for passage before being used for the experiments. HT-29 cells were cultured at a concentration of 2×105 cells/cm2 per well in a 24-well plate, and then, a test drug was pre-treated for 1 hour in a medium supplemented only with 1% FBS and 1% PS. Next, 10 μg/mL BCECF-AM was treated therewith to allow a reaction at a temperature of 37° C. for 30 minutes. Afterwards, the HT-29 cells, which were previously treated with the test drug, were allowed to react with U937 cells in which BCECF was loaded, or with TNF-α (10 ng/mL) or interleukin (IL)-6, at a temperature of 37° C. for 3 hours. After the completion of the reaction, the medium of the HT-29 cells was removed, and then, the HT-29 cells were washed with PBS twice, thereby removing U937 cells that were not adhered to the HT-29 cells. Next, in terms of cell dissolution, 0.1% Triton X-100 (0.1 M Tris) was allowed to react with the cells for 30 minutes at room temperature, and then, the the cells were subjected to quantify by measuring fluorescence thereof using a Fluostar optima microplate reader (BMG Labtechnologies, Germany) (Carvalho et al., 1996; Thapa et al., 2008).

2. Results

The results of analyzing inhibitory activity of the test drug (1 μM) against the adhesion to the TNF-α-induced intestinal epithelial cells (i.e., HT-29) and the mononuclear cells (i.e., U937) are shown in Table 2, and the results of analyzing inhibitory activity of the test drug (1 μM) against the adhesion to the IL-6-induced intestinal epithelial cells (i.e., HT-29) and the mononuclear cells (i.e., U937) are shown Table 4. In the case mesalazine (a positive control), which is an active metabolite of sulfasalazine that is a drug in use for the treatment of inflammatory bowel disease in current clinical, mesalazine showed a inhibition rate of 6% or less against the adhesion between the TNF-α-induced intestinal epithelial cells (i.e., HT-29) and the mononuclear cells (i.e., U937), and that is, mesalazine hardly exhibited the inhibitory effect (see Table 3). However, in the case of 13 types of aminopyridinol compounds, the compounds showed an inhibition rate of 50% or more at 1 μM concentration, and more particularly, aminopyridinol compound 11 exhibited significantly excellent inhibition rates of 80% or more. Aminopyridinol compounds 7, 9, 10, 12, 19 and 34 showed inhibition rates between 70~79%, aminopyridinol compounds 30, 32, 33 and 35 showed inhibition rates between 60~69%, and aminopyridinol compounds 31 and 38 showed inhibition rates between 50~59%. In addition, aminopyridinol compounds 20, 23, 28, 29, 36 and 37 showed inhibition rates between 40~49%, aminopyridinol compounds 4, 6, 8, 13, 25 and 27 showed inhibition rates between 30~39%, aminopyridinol compounds 1, 2, 3, 14, 16, 17, 21 and 22 showed inhibition rates between 20~29%, and aminopyridinol compounds 5, 15, 18, 24 and 26 showed inhibition rates of less than 20%. Accordingly, it was confirmed that the compounds having inhibition rates of less than 20% mostly exhibited better inhibitory activity than that of mesalazine.

Regarding the inhibitory effects of mesalazine against adhesion between the IL-6-induced intestinal epithelial cells (i.e., HT-29) and mononuclear cells (i.e., U937), mesalazine hardly exhibited inhibitory activity when having an inhibitory rate of 5% or less at 1 mM concentration (see Table 5). However, 13 types of aminopyridinol compounds showed inhibition rates of 50% or more at 1 μM concentration, and more particularly, aminopyridinol compound 11 exhibited significantly excellent inhibition rates of 70% or more. Aminopyridinol compounds 7, 9, 10, 12, 19, 23, 30 and 34 showed inhibition rates between 60~69%, aminopyridinol compounds 32, 33, 35 and 38 showed inhibition rates between 50~59%, aminopyridinol compounds 29 and 31 showed inhibition rates between 40~49%. In addition, aminopyridinol compounds 20, 28, 36 and 37 showed inhibition rates between 30~39%, aminopyridinol compounds 4, 6, 8, 13, 16, 17, 21, 25 and 27 showed inhibition rates between 20~29%, and aminopyridinol compounds 1, 2, 3, 5, 14, 15, 18, 22, 24 and 26 showed inhibition rates of less than 20%. Accordingly, it was confirmed that the compounds having inhibition rates of less than 20% mostly exhibited better inhibitory activity than that of mesalazine.

TABLE 2

Inhibitory activity against TNF-α-induced monocyte adhesion to colon epithelial cells at 1 μM concentration of aminopyridinols

| Inhibition (%) | Aminopyridinol compounds |
|---|---|
| >80 | 11 |
| 70~79 | 7, 9, 10, 12, 19, 34 |
| 60~69 | 30, 32, 33, 35 |
| 50~59 | 31, 38 |
| 40~49 | 20, 23, 28, 29, 36, 37 |
| 30~39 | 4, 6, 8, 13, 25, 27 |
| 20~29 | 1, 2, 3, 14, 16, 17, 21, 22 |
| <20 | 5, 15, 18, 24, 26 |

TABLE 3

Inhibitory activity of mesalazine (a positive control) against TNF-α-induced monocyte adhesion to colon epithelial cells

| | |
|---|---|
| at 20 mM concentration | 45~55% inhibition |
| at 1 μM concentration | 2~6% inhibition |
| $IC_{50}$ | 15~20 mM |

TABLE 4

Inhibitory activity against IL-6-induced monocyte adhesion to colon epithelial cells at 1 μM concentration of aminopyridinols

| Inhibition (%) | Aminopyridinol compounds |
|---|---|
| >70 | 11 |
| 60~69 | 7, 9, 10, 12, 19, 23, 30, 34 |
| 50~59 | 32, 33, 35, 38 |
| 40~49 | 29, 31 |
| 30~39 | 20, 28, 36, 37 |
| 20~29 | 4, 6, 8, 13, 16, 17, 21, 25, 27 |
| <20 | 1, 2, 3, 5, 14, 15, 18, 22, 24, 26 |

TABLE 5

Inhibitory activity of mesalazine (a positive control) against IL-6-induced monocyte adhesion to colon epithelial cells

| | |
|---|---|
| at 20 mM concentration | 40~45% inhibition |
| at 10 mM concentration | 20~25% inhibition |
| at 1 mM concentration | 1~5% inhibition |
| $IC_{50}$ | 23~27 mM |

<Experimental Example 2> Test on In Vivo Effects of Compounds for Oral Administration Using Animal Models Having Inflammatory Bowel Disease Induced by TNBS 1. Test Method The animals used herein was a 7 to 8 week Sprague Dawley species purchased from OrientBio (Korea). After the purchase, the animals were stabilized with typical solid feed for 7 days before being used for the experiments. The animals were freely supplied with feed and water during the experiments, and stayed in conditions maintaining a cage temperature of about 25±1° C. and relative humidity of about 50±10%. The cage was equipped with an automatic lighting management system to adjust 12-hour light-dark cycle. Regarding experimental groups, 4 groups (i.e., a control group, a group administered with TNBS only, a group administration in combination of TNBS+sulfasalazine 300 mg/kg, and a group administration in combination of TNBS+aminopyridinol 1 mg/kg) were used for the experiment according to the randomized block design, wherein each group consists of 6 rats having an average weight of about 180±10 g.

2. Induction of Enteritis Upon TNBS Rectal Administration

The rats that had been fasting for 24 hours were anesthetized with diethyl ether, and then, a 1 ml syringe connected with a polyethylene catheter was used to slowly inject 5% TNBS into the lumen of the colon through the anus, wherein 5% TNBS was diluted with 50 v/v % ethanol. To prevent leakage of 5% TNBS from the anus, the rats turned upside down and let stand for 60 seconds. Regarding the control group, only a vehicle (50 v/v % ethanol) was injected to the rats of the control group in the same manner as in preparation of other experimental groups (Thapa et al., 2008).

3. Drug Administration

To examine the effects of the drug, the rats were administered with a drug every day at a certain time from the second day to the fifth day of the TNBS treatment.

4. Weight Observation of Rats

Changes in weight of the rats used in the experiments were observed by using a digital mass meter, beginning from the fasting step, the TNBS administration, and the drug administration.

5. Weight Observation of Intestine

After the large intestine of the rat was extracted, a 5 to 6 cm-long tissue therefrom was cut from the anus to a size of 1 cm, and then, subjected to measurement of the tissue weight.

6. Results

Regarding compounds exhibiting excellent inhibitory activity in in vitro adhesion test, inhibitory activity of the compounds against in vivo enteritis was measured, and the results are shown in Table 6.

TABLE 6

Inhibitory effects of aminopyridinols
(1 mg/kg) on TNBS-induced rat colitis

| Compound | Dose (mg/kg) | Colon weight recovery (%) | Body weight recovery (%) |
|---|---|---|---|
| Sulfasalazine | 300 | 68~72 | 48~52 |
| 9 | 1 | 93~97 | 79~83 |
| 12 | 1 | 74~78 | 51~55 |
| 23 | 1 | 83~87 | 60~64 |

(1) Changes in Weight

In an animal model with the rats having a weight ranging from about 180 to about 190 g, having colitis, and causing intestinal inflammation by using 5% TNBS, changes in the weight were regularly observed for 5 days at a certain time, based on the weight of the rats that were not treated with TNBS yet. Consequently, it was confirmed that the control group treated with the vehicle continued to increase the weight of the rate, and that the group treated only with TNBS continued to decrease the weight of the rate, but was slightly recovered on the fifth day. However, the recovered weight of the TNBS-treated group was still significantly smaller than the weight of the rats in the normal group. The weight of the rats in the positive group that was treated with 300 mg/kg of sulfasalazine was slowly recovered, but was still smaller than the vehicle-treated control group. However, the rats in the sulfasalazine-treated group showed a significant increase in the weight thereof, compared to the rats in the group treated only with TNBS, thereby eventually showing excellent weight recovery of about 50%. Even if 1 mg/kg of aminopyridinol compounds 9, 12, and 23 were administered to the rats, significant weight recovery rates of the intestine tissue (51% to 83%) was resulted. The compounds listed in the state of having excellent weight recovery rates are as follows: aminopyridinol compounds 9>23>12.

(2) Morphological Observation

The large intestine that was extracted after the completion of the drug administration for 5 days was observed with the naked eye. Consequently, it was observed that the large intestine of the rats in the TNBS-treated group had swelling and redness, compared to that of the rats in the control group, and in addition, showed appendiceal sweeling, congestion, and synechia of the intestine tissue. In the positive group treated with 300 mg/kg of sulfasalazine, it was confirmed that symptoms observed with the naked eyes and synechia between other organs or inflamed large intestine was significantly inhibited. In the case of the group administered with the aminopyridinol compounds, the symptoms above were significantly improved, compared to the group treated with 300 mg/kg of sulfasalazine.

(3) Measurement of Intestine Weight

After the large intestine of the rat was extracted, a 5 to 6 cm-long tissue therefrom was cut from the anus, and then, subjected to measurement of the tissue weight. Consequently, it was confirmed that the group treated only with TNBS had a significant increase in the weight of the intestine having swelling, compared to the vehicle-treated control group. In the positive control group treated with 300 mg/kg of sulfasalazine, it was confirmed that the weight recovery rate of the intestine tissue was about 70%. In the case of the group administered with the aminopyridinol compounds, regardless of the administration of 1 mg/kg of the compounds, the weight recovery rate of the intestine tissue was about 74% to about 97%. The compounds listed in the state of having excellent recovery rate of the intestine tissue are as follows: aminopyridinol compounds 9>23>12.

<Experimental Example 3> Toxicity Test

Male Balb/c mice were orally administered once with Compound 01 suspended in a 0.5% methylcellose solution, in a dosage of each of 0.5 g/kg, 1 g/kg, and 2 g/kg, and then, for 7 days, the survival rate and body weight of the mice were measured.

After the administration, the death, clinical symptoms, and body weight change of the mice were analyzed, and a hematological examination and a blood biochemical examination were performed. Then, the autopsy of the mice was performed, and abnormality of abdominal cavity organs and thoracic cavity organs was examined.

Examination results show that all the animals did not have distinguishing clinical symptoms or did not die, and even body weight change, blood examination, blood biochemical examination, and autopsy results showed no toxicity change.

As described above, the compounds according to the present invention did not show any toxicity change in mice up to the dosage of 2 g/kg, and accordingly, since the compounds have an oral administration lethal dose (LD50) of 2 g/kg or more, the compounds are considered as a safe material.

Hereinafter, Preparation Examples for the preparation of a composition including Compound 1 will be described. However, the Preparation Examples do not limit the present invention and are presented herein for illustrative purpose only.

<Preparation Example 1> Preparation of Powder Formulation 20 mg of Compound 1, 100 mg of lactose, and 10 mg of talc were mixed, and a sealed bag was filled with the mixture to prepare a powder formulation.

<Preparation Example 2> Preparation of Tablet Formulation 20 mg of Compound 1, 100 mg of corn starch, 100 mg of lactose, and 2 mg of magnesium stearate were mixed, and then, the mixture was compressed according to a conventional tablet preparation method to form a tablet formulation.

<Preparation Example 3> Preparation of Capsule Formulation 10 mg of Compound 1, 100 mg of corn starch, 100 mg of lactose, and 2 mg of magnesium stearate were mixed, and then, the components were mixed according to a conventional capsule preparation method. A gelatin capsule was filled with the result to prepare a capsule formulation.

<Preparation Example 4> Preparation of Injectable Liquid Formulation 10 mg of Compound 1, an appropriate amount of injectable sterilized distilled water, and an appropriate amount of a pH controller were mixed, and then, according to a conventional injectable preparation method, an injectable liquid formulation was prepared including the dosage described above per 1 ample (2 ml).

<Preparation Example 5> Preparation of Ointment Formulation 10 mg of Compound 1, 250 mg of PEG-4000, 650 mg of PEG-400, 10 mg of white vaseline, 1.44 mg of methyl p-hydroxybenzoate, 0.18 mg of propyl p-hydroxybenzoate, and the balance of purified water were mixed, and then, an ointment formulation was prepared according to a conventional ointment preparation method.

It should be understood that the exemplary embodiments described herein should be considered in a descriptive sense only and not for purposes of limitation, and do not limit the scope of the present invention. Accordingly, the substantial scope of the present invention is defined by the following claims and equivalents thereto.

What is claimed is:
1. A method of treating inflammatory bowel disease, comprising:
administering a pharmaceutical composition comprising a 6-aminopyridin-3-ol compound of Formula 1 below or a pharmaceutically acceptable salt thereof as an active ingredient to a subject:

[Formula 1]

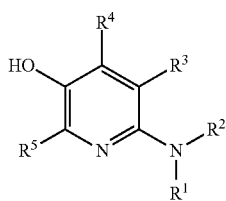

wherein
$R^1$ is a hydrogen, a C1 to C4 alkyl, or a phenyl,
$R^2$ is hydroxy(C1 to C16)alkyl, a (5-hydroxy-trimethyl-pyridin-2-yloxy)-(C2 to C4)alkyl, a C3 to C7 cycloalkyl, a benzyl, a phenyl, a (C1 to C4 alkyl)phenyl, a nitrophenyl, a halophenyl, a benzo[d][1,3]-dioxol-5-yl, or a pyridine-2-yl; or
$R^1$ and $R^2$ are linked to each other to form a 5-membered ring or a 6-membered ring, thereby forming a heterocyclic compound, and are any one selected from pyrrolidine-1-yl, 4-methylpiperazine-1-yl, morpholino, and 1H-pyrrol-1-yl, and
each of $R^3$ to $R^5$ is a methyl.

2. The method according to claim 1, wherein,
$R^1$ is a hydrogen, a C1 to C4 alkyl, or a phenyl,
$R^2$ is a hydroxy(C1 to C6)alkyl, (5-hydroxy-3,4,6-trimethylpyridin-2-yloxy)propyl, a C5 to C6 cycloalkyl, a benzyl, a phenyl, a (C1 to C4 alkyl)phenyl, a nitrophenyl, a halophenyl, or a benzo[d][1,3]-dioxol-5-yl or pyridine-2-yl; or
$R^1$ and $R^2$ are linked to each other to form a 5-membered ring to a 6-membered ring, thereby forming a heterocyclic compound, and are each pyrrolidine-1-yl, 4-methylpiperazine-1-yl, morpholino, or 1H-pyrrol-1-yl, and
each of $R^3$ to $R^5$ is a methyl.

3. The method according to claim 1, wherein the compound or pharmaceutically acceptable salt thereof is selected from the group consisting of 6-(benzylamino)-2,4,5-trimethylpyridin-3-ol; 6-((3-hydroxypropyl)amino)-2,4,5-trimethylpyridin-3-ol; 6-(3-((5-hydroxy-3,4,6-trimethylpyridin-2-yl)amino)propoxy)-2,4,5-trimethylpyridin-3-ol; 6-(cyclopentylamino)-2,4,5-trimethylpyridin-3-ol; 6-(cyclohexylamino)-2,4,5-trimethylpyridin-3-ol; 2,4,5-trimethyl-6-(phenylamino)pyridin-3-ol; 2,4,5-trimethyl-6-(m-tolylamino)pyridin-3-ol; 2,4,5-trimethyl-6-(p-tolylamino)pyridin-3-ol; 2,4,5-trimethyl-6-((4-propylphenyl)amino)pyridin-3-ol; 6-((2-isopropylphenyl)amino)-2,4,5-trimethylpyridin-3-ol; 6-((4-(tert-butyl)phenyl)amino)-2,4,5-trimethylpyridin-3-ol; 6-(benzo[d][1,3]dioxol-5-ylamino)-2,4,5-trimethylpyridin-3-ol; 6-((3-fluorophenyl)amino)-2,4,5-trimethylpyridin-3-ol; 6-((4-fluorophenyl)amino)-2,4,5-trimethylpyridin-3-ol; 6-((3-chlorophenyl)amino)-2,4,5-trimethylpyridin-3-ol; 6-((4-chlorophenyl)amino)-2,4,5-trimethylpyridin-3-ol; 6-((3-bromophenyl)amino)-2,4,5-trimethylpyridin-3-ol; 6-((4-bromophenyl)amino)-2,4,5-trimethylpyridin-3-ol; 2,4,5-trimethyl-6-((3-nitrophenyl)amino)pyridin-3-ol; 2,4,5-trimethyl-6-((4-nitrophenyl)amino)pyridin-3-ol; 2,4,5-trimethyl-6-(pyridin-2-ylamino)pyridin-3-ol; 2,4,5-trimethyl-6-(pyrrolidin-1-yl)pyridin-3-ol; 2,4,5-trimethyl-6-(4-methylpiperazin-1-yl)pyridin-3-ol; 2,4,5-trimethyl-6-morpholinopyridin-3-ol; 2,4,5-trimethyl-6-(methyl(phenyl)amino)pyridin-3-ol; 2,4,5-trimethyl-6-(methyl(m-tolyl)amino)pyridin-3-ol; 2,4,5-trimethyl-6-(methyl(p-tolyl)amino)pyridin-3-ol; 6-((4-fluorophenyl)(methyl)amino)-2,4,5-trimethylpyridin-3-ol; 6-((4-chlorophenyl)(methyl)amino)-2,4,5-trimethylpyridin-3-ol; 6-(diphenylamino)-2,4,5-trimethylpyridin-3-ol; 2,4,5-trimethyl-6-(methyl(pyridin-2-yl)amino)pyridin-3-ol and 2,4,5-trimethyl-6-(1H-pyrrol-1-yl)pyridin-3-ol.

4. The method according to claim 1, wherein the pharmaceutically acceptable salt is an acid-added salt from an organic acid selected from the group consisting of an oxalic acid, a maleic acid, a fumaric acid, a malic acid, a tartaric acid, a citric acid, a benzoic acid, methanesulfonic acid and camphorsulfonic acid.

5. The method according to claim 1, wherein the pharmaceutically acceptable salt is an acid-added salt from an inorganic acid selected from the group consisting of a hydrochloric acid, a sulfuric acid, a phosphoric acid, and a hydrobromic acid.

6. A method of treating inflammatory bowel disease, comprising:
   administering a pharmaceutical composition comprising a 6-aminopyridin-3-ol compound or a pharmaceutically acceptable salt thereof as an active ingredient to a subject,
   wherein the 6-aminopyridin-3-ol compound is selected from the group consisting of 6-((4-methoxyphenyl)amino)-2,4,5-trimethylpyridin-3-ol, 6-((3-isopropoxyphenyl)amino)-2,4,5-trimethylpyridin-3-ol, and 2,4,5-trimethyl-6-(piperidin-1-yl)pyridin-3-ol.

* * * * *